United States Patent [19]
Patag et al.

[11] Patent Number: 6,035,239
[45] Date of Patent: Mar. 7, 2000

[54] CARDIAC LEAD WITH REDUCED INNER CRIMP SLEEVE

[75] Inventors: Alfredo E. Patag, Lake Jackson; Florence A. Kane, Angleton; James E. Machek, Lake Jackson, all of Tex.

[73] Assignee: Intermedics Inc., Angleton, Tex.

[21] Appl. No.: 09/189,648

[22] Filed: Nov. 10, 1998

[51] Int. Cl.[7] .................................................... A61N 1/05
[52] U.S. Cl. .............................................................. 607/122
[58] Field of Search ................................... 607/122, 123, 607/115, 116, 119

[56] References Cited

U.S. PATENT DOCUMENTS

| | | |
|---|---|---|
| 5,115,818 | 5/1992 | Holleman et al. . |
| 5,257,634 | 11/1993 | Kroll ........................................ 607/122 |
| 5,476,500 | 12/1995 | Fain et al. ................................ 607/126 |

*Primary Examiner*—Scott M. Getzow
*Attorney, Agent, or Firm*—Schwegman, Lundberg, Woessner & Kluth P.A.

[57] ABSTRACT

A cardiac lead includes a connector for coupling to a cardiac stimulator and a flexible insulating sleeve having a first end coupled to the connector. An inner crimp sleeve is coupled to the insulating sleeve and an outer crimp sleeve crimped around the inner crimp sleeve. A first conductor wire is provided that has at least a first loop and a second loop. A second conductor wire is provided that has a third loop. The first and second conductor wires are spiraled together so that the third loop is positioned between the first and second loops and is crimped between the inner crimp sleeve and the outer crimp sleeve. The arrangement eases the passage of a stylet past the union of two wires, reducing the potential for stylet buckling. An aperture is provided in the outer crimp sleeve.

23 Claims, 10 Drawing Sheets

CARDIAC LEAD WITH REDUCED INNER CRIMP SLEEVE

BACKGROUND OF THE INVENTION

1. Field of the Invention

This invention relates generally to cardiac stimulator leads, and more particularly to a cardiac stimulator lead having a crimp assembly for joining the ends of two conductor wires.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

A conventional cardiac stimulator lead normally consists of an elongated flexible tubular, electrically insulating sleeve that is connected proximally to a connector that is adapted to couple to the header of a cardiac stimulator. In pacing leads, the distal end of the insulating sleeve is joined with a tip electrode. In defibrillator leads, a defibrillator or shock coil commonly projects from the distal end of the insulating sleeve. The shock coil consists of an uninsulated coiled wire wound with a large number of coils or loops. The plurality of loops distribute defibrillation pulses over a much larger surface area of the myocardium than a pacing electrode.

In some conventional defibrillator lead designs, the electrical pathway between the lead connector and the shock coil is provided by a separate conductor wire that is coupled proximally to the connector and secured distally to a crimp assembly. The conventional crimp assembly consists of an inner tubular sleeve over which respective ends of the shock coil and the other conductor wire are positioned and crimped into position by respective outer crimp sleeves. The inner sleeve and the outer sleeves are normally made of titanium or other relatively rigid biocompatible conducting materials. The inner tubular sleeve is of such length that the ends of the shock coil and the other wire are usually not intertwined. The conducting nature of the inner sleeve is relied upon to pass current between the two wires.

A conventional crimp assembly can significantly hamper the movement of a stylet used to spatially manipulate the lead during implantation. For most implantation procedures, the physician inserts a stylet into the lead connector and advances it to the distal tip of the lead. The physician then manipulates the stylet to accurately position the distal end of the lead proximate the endocardial site requiring electrical stimulation. The distal end of the stylet must be inserted through the crimp assembly in order to reach the tip of the lead. This step may not be problematic where the stylet is not bent significantly prior to insertion, as is often the case where the implantation involves a relatively straight pathway through the heart. Fixation to the right ventricular apex is an example of such a relatively straight pathway.

Where the implantation requires the pathway of the lead tip to be deviated, the situation may become more difficult for the physician. For example, fixation to the superior interventricular septum or access to the great cardiac vein via the coronary sinus require the lead tip to be turned abruptly after entry into the heart. This is frequently accomplished by introducing a severe bend in the distal end of the lead, usually after the lead is initially positioned inside the heart. Initially, a straight stylet is used to move the lead into the right atrium. Then the straight stylet is removed and a highly curved stylet is inserted and advanced to the distal end of the lead. The stylet is usually curved by the physician by hand based on the physician's experience and knowledge of the patient's particular anatomy. The radius of curvature of the bend may be quite small.

The initial movement of the highly curved portion of the stylet through the lead may be unremarkable since the majority of the lead is quite flexible. As the curved portion is advanced, the lead is able to temporarily conform to the curvature of the stylet. In contrast to the insulating sleeve, the crimp assembly is quite rigid and cannot conform to the curvature of the stylet. As a result, the physician may encounter significant resistance to further axial movement when the highly curved portion of the stylet encounters the inner sleeve. This undesirable tactile response is more than just a nuisance. The natural tendency of the physician at this point is to apply additional thrust to the proximal end of the stylet to force the curved portion through the inner sleeve. Because the stylet is highly curved and thrust is being applied at the opposite end thereof, the stylet will tend to behave like an unstable column under compression loading. If the rubbing of the inner sleeve is great enough, axial thrust applied by the physician will cause the stylet to buckle and plastically deform at one or more points along its length. With one or more unintended bends in the stylet, the movement of the lead in response to manipulation of the stylet may be unpredictable and the complexity of the implantation procedure increased.

The present invention is directed to overcoming or reducing the effects of one or more of the foregoing disadvantages.

SUMMARY OF THE INVENTION

In accordance with one aspect of the present invention, a cardiac lead is provided. The cardiac lead includes a connector for coupling to a cardiac stimulator and a flexible insulating sleeve having a first end coupled to the connector. An inner crimp sleeve is placed over the insulating sleeve. A first conductor wire is provided that has at least a first loop and a second loop. A second conductor wire is provided that has at least a third loop. The first and second conductor wires are spiraled together so that the third loop is positioned between the first and second loops and the intertwined first, second and third loops encircle the inner crimp sleeve. An outer crimp sleeve is positioned over the first, second and third loops and crimped to secure both conductor wires.

In another aspect of the invention the outer crimp sleeve has an aperture for viewing both conductor wires during assembly. Both conductor wires are secured by a single crimp. In accordance with yet another aspect of the invention, the length of the crimp sleeve assembly comprising the assembled inner and outer crimp sleeves, is reduced to 7.2 mm (0.3 inches) or less.

In accordance with another aspect of the present invention, a cardiac lead is provided. The cardiac lead includes a branch assembly, a first connector and a second connector coupled to the branch assembly. An inner crimp sleeve is positioned in the branch assembly. A first conductor wire is coupled to the first connector and has at least a first loop and a second loop. A second conductor wire is coupled to the second connector and has at least a third loop. The first and second conductor wires are spiraled together so that the third loop is positioned between the first and second coils and the three loops are positioned around the inner crimp sleeve. An outer crimp sleeve is positioned around the first sleeve over the first, second and third loops. The three loops are crimped between the inner crimp sleeve and the outer crimp sleeve.

In accordance with another aspect of the present invention, a cardiac lead is provided. The cardiac lead includes a connector for coupling to a cardiac stimulator and a first conductor wire is provided that has a first end coupled to the connector and a second end that has at least a first loop and a second loop. A second conductor wire is provided that has a third end that has at least a third loop and a second end that has a plurality of loops positioned in spaced-apart relation to the first conductor wire. The first and second conductor wires are spiraled together so that the third loop is positioned between the first and second loops. The loops crimped between an inner crimp sleeve and an outer crimp sleeve.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Background Art

Figure 1:
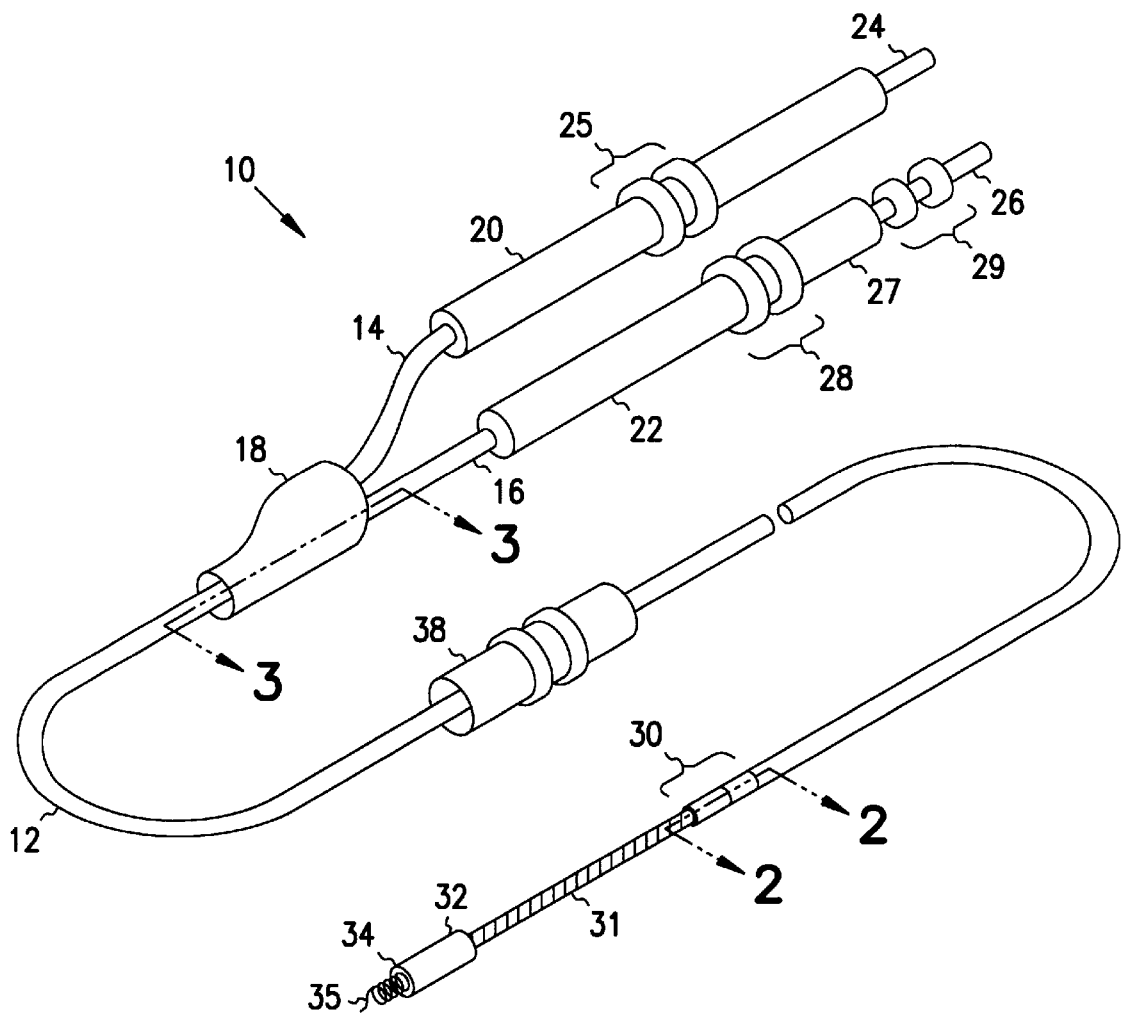
FIG. 1 is a pictorial view of a conventional cardiac stimulator lead.
Figure 2:
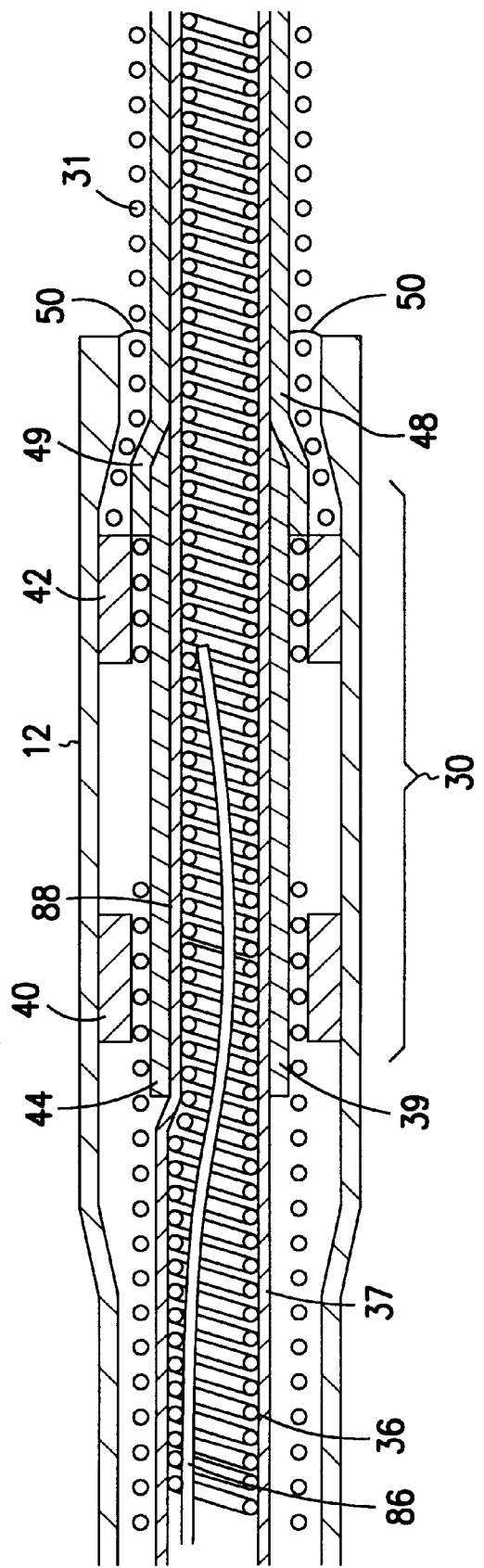
FIG. 2 is a cross-sectional view of FIG. 1 taken at section 2—2.

Turning now to the drawings, and in particular to FIGS. 1 and 2 there is shown an exemplary conventional pacing/defibrillator lead 10 (hereinafter "lead 10"). The lead 10 is provided with a flexible tubular insulating sleeve 12 that divides proximally into segments 14 and 16 at a branch 18. The segment 14 terminates proximally in a connector 20 and the segment 16 terminates proximally in another connector 22. The connectors 20 and 22 are designed to be inserted into a cardiac pacemaker can (not shown). The connector 20 terminates proximally in a pin 24. The pin 24 is connected to a conductor wire positioned inside the segment 14 and the lead sleeve 12 as described more fully below. A set of O-rings 25 is molded to the exterior of the connector 20 to retard the intrusion of body fluids into the pacemaker can. The connector 22 similarly terminates in a connector pin 26. However, the pin 26 is hollow to enable insertion of a stylet inside the lead 10 during implantation. The connector pin 26 is connected to a conductor wire that is positioned in the segment and stretches to the branch 18 as described more fully below. An annular contact 27 is fitted to the connector 22. Pairs of O-rings 28 and 29 are molded to the exterior of the connector 22 to prevent the intrusion of body fluids.

The distal end of the insulating sleeve 12 encloses a crimp assembly 30. A defibrillator or shock coil 31 projects distally from the crimp assembly 30, terminating inside a tip sleeve 32. A tip electrode 34 projects slightly from the tip sleeve 32 and is provided with a corkscrew 35 for securing the lead 10 to myocardial tissue. The tip electrode 34 is connected to a conductor wire 36 that extends through the length of the lead 10, terminating at and connecting with the pin 26. The conductor wire 36 is jacketed by an insulating sleeve 37 that is secured distally to the tip electrode 34 by a biocompatible medical grade adhesive and proximally over the connector pin 26 in a like manner. A suture sleeve 38 is slipped over the sleeve 12.

The detailed structure of the crimp assembly 30 may be understood by referring to FIG. 2 The crimp assembly 30 includes an inner crimp sleeve 39 that is positioned inside the insulating sleeve 12. Two outer crimp sleeves 40 and 42 are crimped around the inner crimp sleeve 39. Each outer crimp sleeve secures a single conductor wire, although conductor wire may comprise multiple filars. The outer crimp sleeve 40 secures the distal end of a conductor wire 44 to the inner crimp sleeve 39. Similarly, the outer crimp sleeve 42 secures the proximal end of the shock coil 31 to the inner crimp sleeve 39. The inner crimp sleeve 39 is typically composed of a conducting material, such as titanium, that establishes an electrical pathway between the distal end of the conducting wire 44 and the proximal end of the shock coil 31. The conductor wire 36 passes through the inner crimp sleeve 39 and is connected proximally to the connector pin 26 of the connector 22, and distally to the tip electrode 34 shown in FIG. 1. The shock coil 31 is disposed around a shock coil sleeve 48. One end 49 of the shock coil sleeve 48 is slipped over the distal end of the inner crimp sleeve 39. The other end is secured to the proximal end of the tip electrode 34 shown in FIG. 1.

The insulating sleeve 12 is slipped around the exterior of the inner crimp sleeve 39 between the outer crimp sleeves 40 and 42, and secured with medical adhesive. The small gap between the inner diameter of the insulating sleeve 12 and the outer diameter of the shock coil sleeve 48 is sealed with a biocompatible adhesive 50. The conductor wire 44 is individually insulated, save the portion thereof positioned between the outer crimp sleeve 40 and the inner crimp sleeve 39 so that electrical isolation is maintained between the conductor wire 44 and the conductor wire 36 throughout the length of the insulating sleeve 12.

Figure 3:
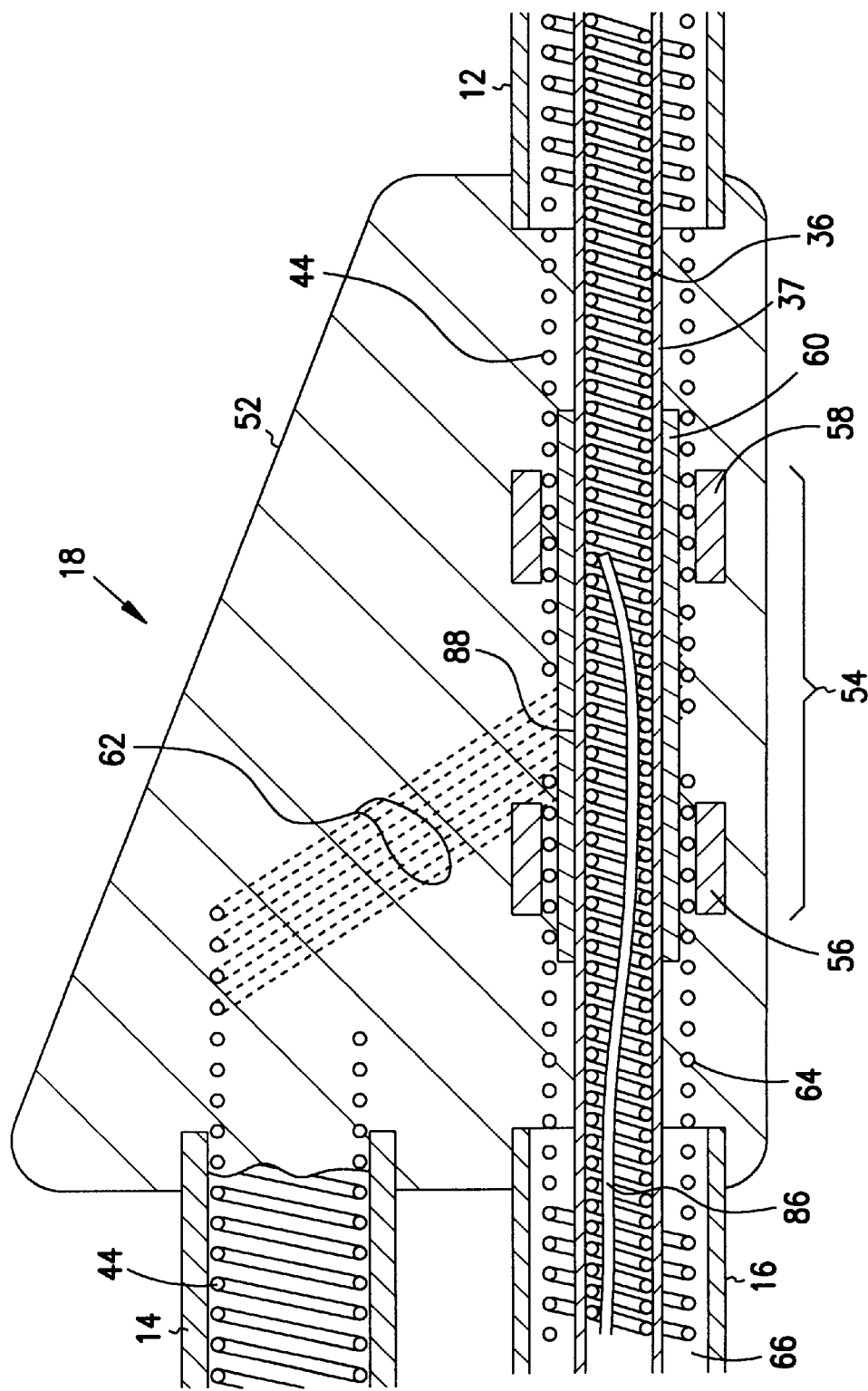
FIG. 3 is a cross-sectional view of FIG. 1 taken at section 3—3.

The detailed structure of the branch 18 may be understood by referring now to FIG. 3, which is a cross sectional view of FIG. 1 taken at section 3—3. The branch 18 includes a branch body 52 that is slipped over and glued around the segment 14, the segment 16 and the insulating sleeve 12 as shown. A crimp assembly 54 is positioned inside the branch body 52 and is structurally identical to the crimp assembly 30 depicted in FIG. 2. Accordingly, the crimp assembly 54 includes outer crimp sleeves 56 and 58 positioned around an inner crimp sleeve 60. The conductor wire 44 is crimped to the inner crimp sleeve 56 by the outer crimp sleeve 58. Proximal to the outer crimp sleeve 58, the conductor wire 44 is uncoiled and routed through the branch body 52 and into the segment 14. The uncoiled filars 62 of the conductor wire 40 are shown in phantom. The distal end of a conductor wire 64 is crimped to the inner crimp sleeve 60 by the outer crimp sleeve 56. The conductor wire 64 is connected proximally to the annular electrode 27 of the connector 22 shown in FIG. 1. Note that the conductor wire 64 and the conductor wire 44 are electrically connected via the conducting inner crimp sleeve 60. The conductor wire 36 passes through the branch body 52 and the inner crimp sleeve 60 and into a tubular sleeve 66 that is positioned inside the segment 16 and extends proximally past the proximal end of the annular electrode 27.

Figure 4:
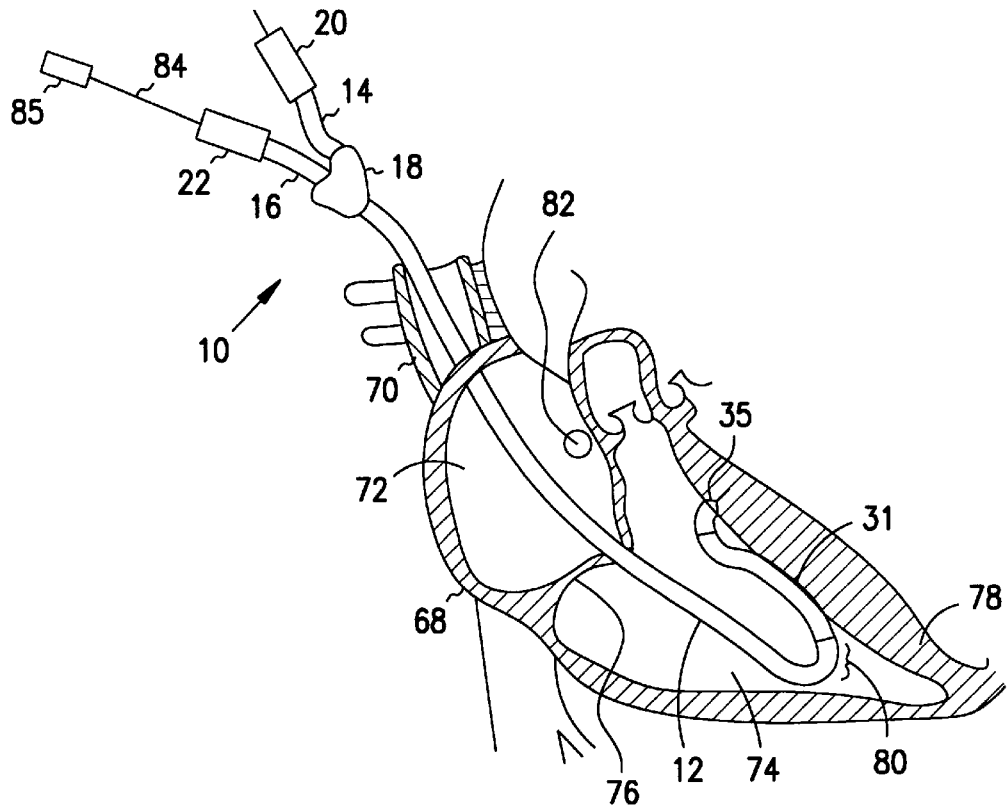
FIG. 4 is a quarter-sectional anterior view of a human heart depicting a typical implantation of the lead shown in FIGS. 1–3.
Figure 5:
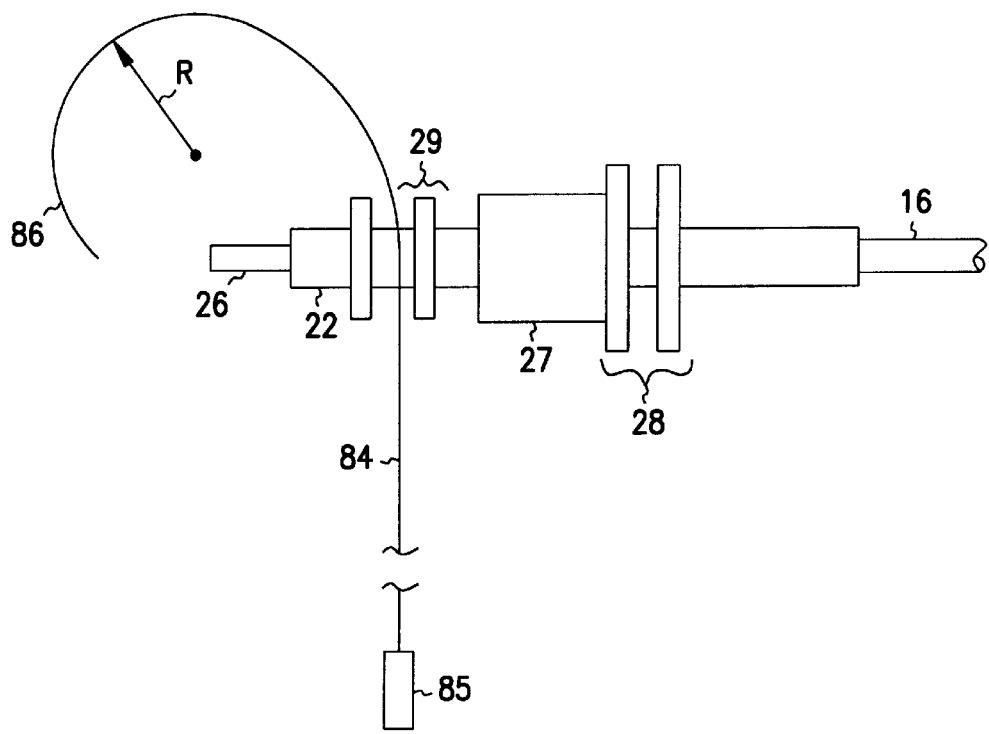
FIG. 5 is a side view of the proximal end of the lead of FIG. 1 depicting insertion of a curved stylet.

An illustrative implantation of the lead 10 may be understood by referring now to FIGS. 4 and 5. FIG. 4 is a quarter-sectional anterior view of a human heart 68. The lead sleeve 12 is introduced into the superior cava 70, and advanced through the right atrium 72 into the right ventricle 74 via the tricuspid valve 76. The corkscrew 35 of the lead 10 is secured superiorly to the interventricular septum 78 and a sufficient portion of the lead sleeve 12 is advanced into the right ventricle 74 so that the shock coil 31 is brought into physical engagement with the interventricular septum 78. In order to establish the requisite engagement with the superior interventricular septum 78, a significant bend 80 must be introduced into the lead 10. Bends in the lead 10, such as the bend 80, are common in implantation procedures involving deviated pathways, such as the pathway depicted in FIG. 4, as well as pathways leading to fixation to the right hand side of the right atrium 68 or pathways involving entry into the coronary sinus 82.

The lead 10 is spatially manipulated by means of a flexible stylet 84 that is inserted into the connector pin 26 of the connector 22 and advanced inside the lead 10 to the tip assembly 32. The stylet 84 is of such length that it is shown broken. A small cylindrical handle 85 is fitted to the stylet 84 to aid the physician in applying thrust to the stylet 84, particularly when a majority of the length of the stylet 84 is already inserted into the lead 10. In order to establish the tight bend 80 in the lead 10, the distal end 86 of the stylet 84 is plastically deformed by hand into a highly curved shape prior to insertion into the pin 26 as shown in FIG. 5. The bending action establishes a relatively small radius of the curvature r for the distal end 86.

The tight bend of the distal end 86 combined with the internal structure of the lead 10 can create difficulties for the physician at the time of implantation. Referring again to FIGS. 2 and 3, as the distal end 86 of the stylet 84 is advanced through the connector 22, the segment 16, and into the branch assembly 18, the generally tubular structure of the connector 22 and the inner sleeve 66 will tend to temporarily and partially straighten the distal end 86. However, the distal end 86 will retain a significant curved portion 88 as shown in FIG. 3. As this highly curved portion 88 passes through the inner crimp sleeve 60, significant rubbing and frictional resistance to longitudinal movement will result. Since the inner crimp sleeve 60 is composed of a relatively rigid material, it cannot temporarily deform to more easily permit the curved portion 88 to pass there through.

The resistance to longitudinal movement of the distal end 86 of the stylet 84 through the crimp assembly 54 is normally overcome by applying additional thrust to the portion of the stylet 84 projecting from the connector pin 26 without undue effort. However, the passage of the distal end 86 through the crimp assembly 30 is more problematic. As shown in FIG. 2, as the curved portion 88 of the distal end 86 passes through the crimp assembly 30, the aforementioned rubbing action occurs. The resistance to longitudinal movement of the stylet 84 is now compounded by friction between the stylet 84 and the internal structures of the sleeve 10 proximal to the crimp assembly 30. At this point, the stylet 84 behaves much like an unstable column under compressive load. As thrust is applied to the handle 85 of the stylet 84, and transmitted through the entire length of the extremely thin stylet 84, the stylet 84 will have a tendency to buckle and permanently deform at one or more places between the handle 85 and the highly curved portion 88. These new bends in the stylet 84 can make the behavior of the stylet 84 and the movement of the lead 10 thereby somewhat unpredictable for the physician.

Exemplary Embodiment

Figure 6:
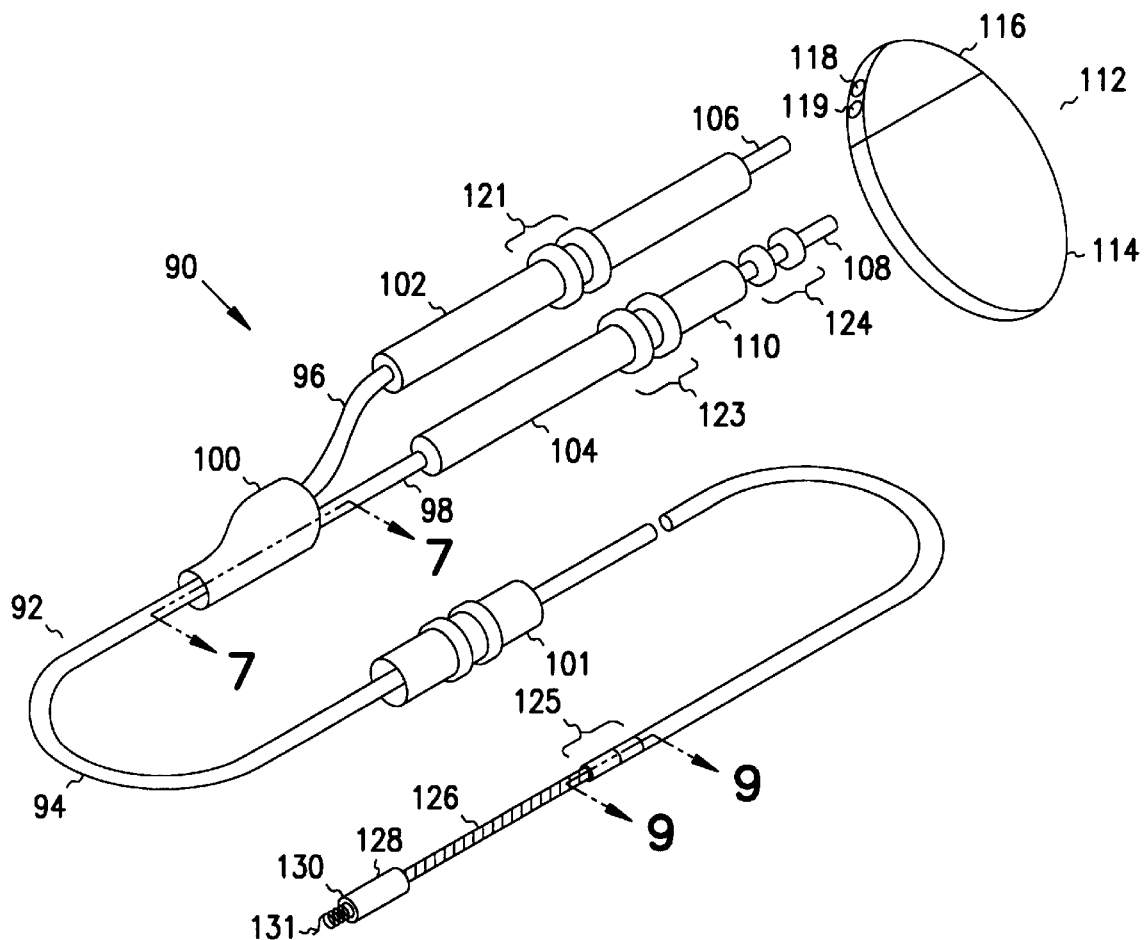
FIG. 6 is pictorial view of an exemplary embodiment of a cardiac lead and a cardiac stimulator in accordance with the present invention.
Figure 7:
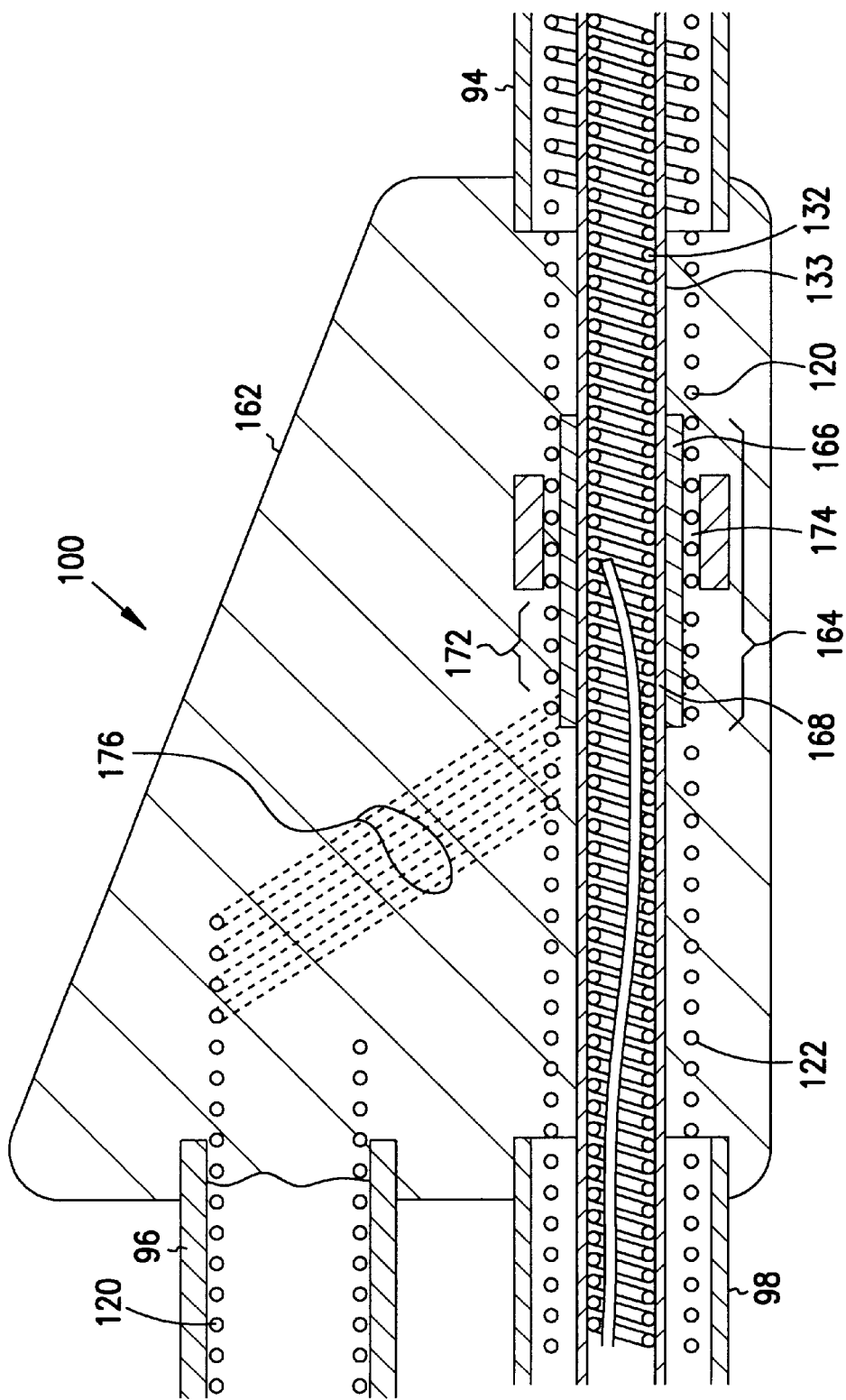
FIG. 7 is a cross-sectional view of FIG. 6 taken at section 7—7 in accordance with the present invention.
Figure 9:
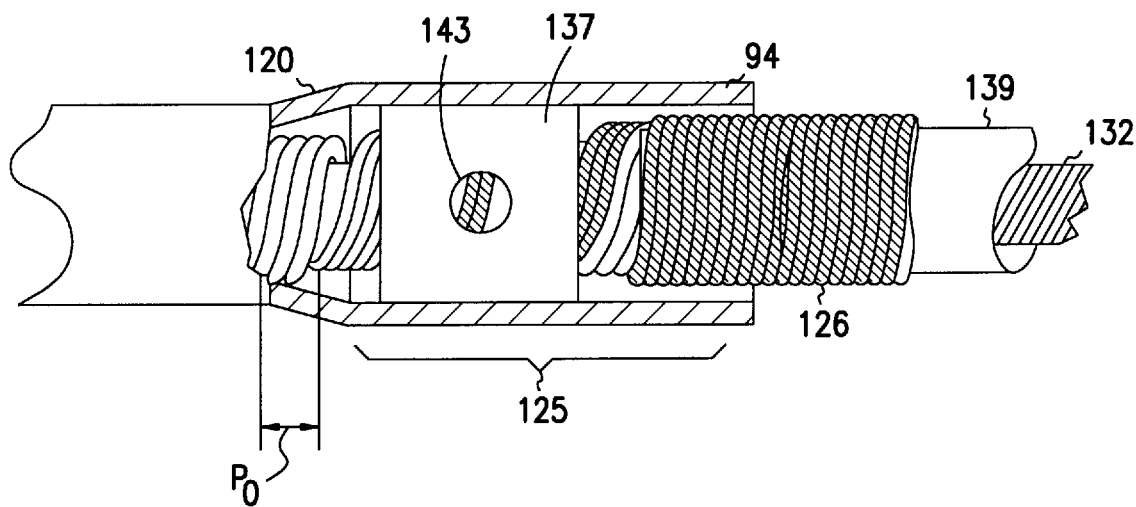
FIGS. 9–11 are cross-sectional views of FIG. 6 taken at section 9—9 with various components shown alternatively in section and in full in accordance with the present invention.

An exemplary embodiment of a cardiac stimulator lead 90 in accordance with the present invention may be understood by referring now to FIGS. 6, 7 and 9. FIGS. 7 and 9 are sectional views of FIG. 6 taken, respectively, at sections 7—7 and 9—9. The cardiac stimulator lead 90 includes a lead body 92 that has a tubular insulating sleeve 94 which bifurcates proximally into two segments 96 and 98 at a branch assembly 100. The length of the lead body 92 is such that it is shown broken. A suture sleeve 101 is slipped over and used to secure the lead body 92 at a preselected point in the patient's body. The segment 96 terminates in a connector 102 and the segment 98 terminates in a connector 104. The connector 102 is provided with a connector pin 106 and the connector 104 is provided with a connector pin 108 and an annular contact 110. The connectors 102 and 104 are designed to be connected to a cardiac stimulator 112, which consists of a can 114 and a header assembly 116 coupled to the can 114. The header assembly 116 includes ports 118 and 119 into which the connectors 102 and 104 are inserted respectively. The connectors 102 and 104 are shown highly exaggerated in size relative to the remainder of the lead 90 for clarity of illustration. The cardiac stimulator 112 may be a pacemaker, a cardioverter/defibrillator, a sensing instrument, or a combination of these functionalities.

The pin 106 is connected via by crimping, welding or the like to a conductor wire 120 that passes through the segment 96 and the branch assembly 100 and extends into the lead sleeve 94 as described more fully below. A set of O-rings 121 is molded to the exterior of the connector 102 to retard the intrusion of body fluids into the cardiac stimulator header 116. The pin 108 is hollow to enable insertion of a stylet inside the lead 90 during implantation. The connector pin 108 is connected by crimping, welding or the like to a conductor wire 122 that passes through the segment 98 and terminates in the branch assembly 100 as described more fully below. Pairs of O-rings 123 and 124 are molded to the exterior of the connector 104 to retard body fluid intrusion. The exterior of the connectors 102 and 104 may be composed of a biocompatible electrically insulating material, such as silicone, polyurethane or the like, and the pins 106 and 108 may be fabricated from stainless steel, titanium or the like.

As shown in FIGS. 6 and 9, the distal end of the insulating sleeve 94 encloses a crimp assembly 125. The insulating sleeve 94 is slipped around the exterior of the crimp assembly and is secured thereto with medical adhesive. A defibrillator or shock coil 126 projects distally from the crimp assembly 125, terminating inside a tip sleeve 128. The shock coil 126, as the names implies, is designed to deliver defibrillating pulses from the cardiac stimulator 112 to myocardial tissue. A tip electrode 130 projects slightly from the tip sleeve 128 and is provided with a corkscrew 131. The corkscrew 131 is used to secure the tip electrode 130 to myocardial tissue, and may be augmented and/or substituted with one or more radially spaced tines or other type of fixation mechanism. The tip electrode 130 is provided to supply pacing pulses from the cardiac stimulator 112 to myocardial tissue and to transmit sensing signals from myocardial tissue back to the cardiac stimulator 112. An electrical pathway between the tip electrode 130 and the connector pin 108 is established by a conductor wire 132 that is connected distally to the tip electrode 130 via by crimping, welding or the like, and extends through the length of the lead 90, terminating at and connecting to the pin 108 by like methods. The conductor wire 132 is jacketed by an insulating sleeve 133 that is secured distally to the tip electrode 130 by a biocompatible medical grade adhesive and proximally over the connector pin 108 in a like manner.

The insulating sleeve 94 is designed to provide a flexible connection between the tip electrode 130 and the shock coil 126 and the connectors 102 and 104 as well as provide electrical insulation for conductors disposed inside the insulating sleeve 94 to be described below. Accordingly, the insulating sleeve 94 is advantageously a flexible tubular structure composed of a biocompatible material, such as silicone, polyurethane or the like. In an exemplary embodiment, the insulating sleeve 94 is composed of silicone. The sleeve 133 may be composed of like materials.

The tip electrode 130 may be fabricated from a variety of biocompatible conducting materials, such as iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material.

Figure 8:
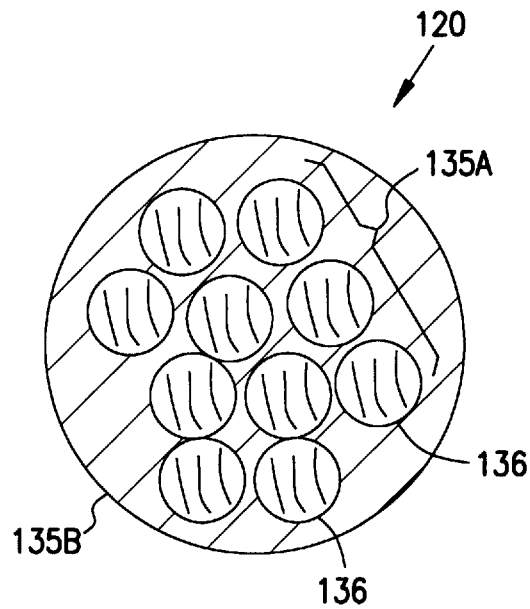
FIG. 8 is a cross-sectional view of one of the filars of a conductor wire of the lead shown in FIGS. 6 and 7 in accordance with the present invention.

The detailed structure of the conductor wire 120 may be understood by referring now also to FIG. 8, which is a cross sectional view of one of the filars of the wire 120. The conductor wire 120 is a four-filar coiled wire, with each filar consisting of a conductor 134 individually coated with an insulating jacket 135. The conductor 134 may include a plurality of filaments 136 as shown or a single filament. The conductor 134 may be composed of a variety of biocompatible conducting materials, such as MP35N, stainless steel, titanium or like materials. In an exemplary embodiment, the conductor 134 is composed of drawn-brazed strands ("DBS") or filaments 136 of stainless steel. The insulating coating 135 may be composed of a variety of biocompatible insulating materials, such as ETFE (fluoropolymer resin) or like materials. The skilled artisan will appreciate that another form of conductor wire may be used, such as, for example, a single filar insulated or uninsulated wire.

The shock coil 126 is a three-filar coiled wire. The filars may be composed of a variety of biocompatible conducting materials, such as MP35N, stainless steel, titanium or like materials. In an exemplary embodiment, the filars are composed of iridium oxide coated titanium. Iridium oxide provides excellent resistance to corrosion caused by body fluids. As with the conductor wire 120, the skilled artisan will appreciate that the shock coil 126 may take on another form, such as, for example, a six filar wire.

Figure 10:
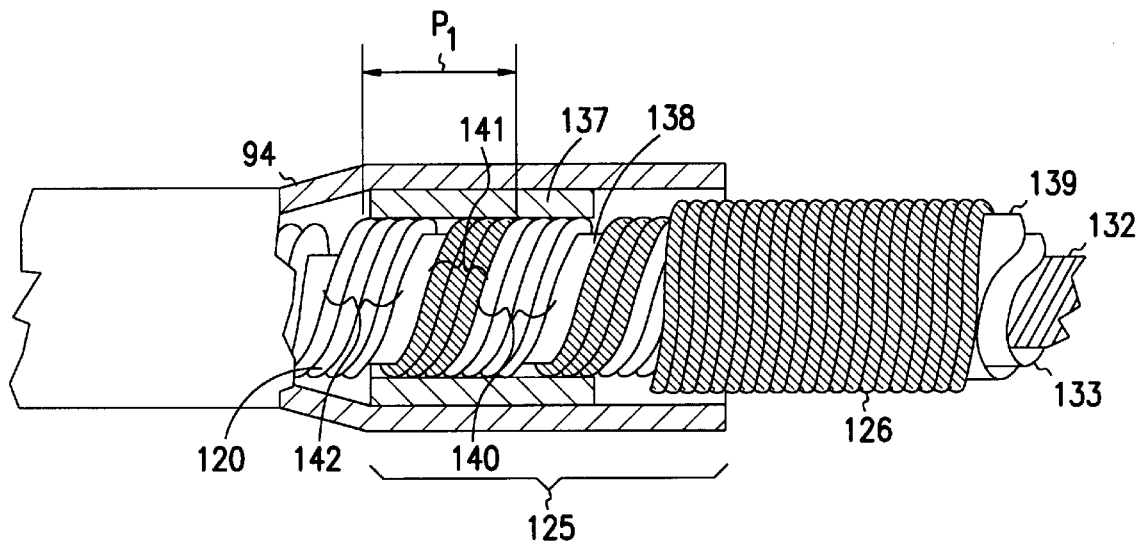
Figure 11:
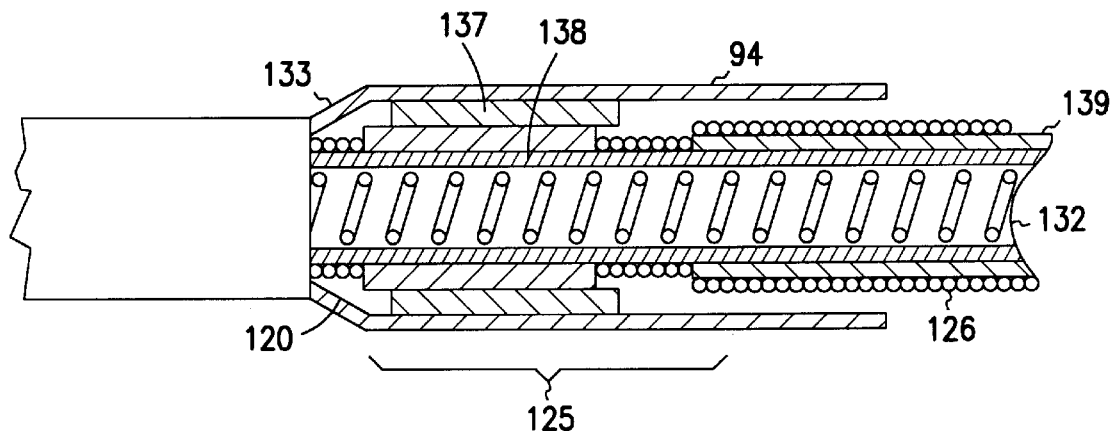

The detailed structure of the crimp assembly 125 may be understood by referring now to FIGS. 9, 10 and 11, which are cross-sectional views of FIG. 6 taken at section 9—9 that show various components alternatively in full and section for clarity of illustration. The crimp assembly 125 includes an outer crimp sleeve 137 positioned around and crimped to an inner crimp sleeve 138 (best seen in FIG. 10) to anchor both the distal end of the conductor wire 120 and the proximal end of the shock coil 126. The term "crimped" is intended to mean crimped, swaged, or otherwise secured. The portion of the wire 120 positioned between the outer crimp sleeve 137 and the inner crimp sleeve 138 is stripped of insulation to establish ready electrical contact with the outer crimp sleeve 137 and the shock coil 126. To provide flexible structural support for the shock coil 126, a flexible tubular extension sleeve 139 is positioned inside the shock coil 126 and coupled proximally over the distal end of the inner crimp sleeve 138 by a biocompatible medical grade adhesive and distally over the proximal end of the tip electrode 132 (see FIG. 6) by a like adhesive. The extension sleeve 139 may be composed of the same types of material used to fabricate the insulating sleeve 94 and gives the shock coil a greater surface area. See, for example, Fine et al., U.S. Pat. No. 4,922,927, incorporated herein by reference. The shock coil 126 is slid over the extension sleeve 139 and at least one loop at the proximal end of the expansion tube 164 is drawn apart manually over the inner crimp sleeve 138. This reduces the diameter of the loops, bringing them into circumferential contact with the inner crimp sleeve 138, and spreads at least two adjacent loops apart from each other.

A distal end of the conductor wire 126 is expanded on a mandrel 144 as described below. An outer crimp sleeve 137 is placed on the conductor wire 126. The expanded distal end of the conductor wire 120 and the proximal end of the shock coil 126 are intertwined by placing a loop of the shock coil 126 between two adjacent loops of the conductor wire 126.

The outer and inner crimp sleeves 137 and 138 are tubular members designed to be crimpable to provide a secure anchoring of the wires 120 and 126. Electrical conductivity is not required as the wires 120 and 126 are in physical contact, but one or both may be conducting. Accordingly, the outer and inner crimp sleeves 137 and 138 may be composed of a variety of biocompatible materials, such as titanium, MP35N, stainless steel, or the like. In an exemplary embodiment, the sleeves 137 and 138 are composed of titanium.

In contrast to the above-described conventional crimp assembly 30 (see FIG. 2), the crimp assembly 125 of the present invention includes a single outer crimp sleeve 137 and a single inner crimp sleeve 138 that is substantially shorter than the conventional inner crimp sleeve 39 (see FIG. 2). To enable the outer and inner crimp sleeves 137 and 138 to reliably secure the conductor wire 120 and the shock coil 126, at least one of the loops 140 of the conductor wire 120 and at least one of the loops 141 of the shock coil 126 are intertwined around the inner crimp sleeve 138 as best seen in FIG. 10. The intertwining of the loops 140 of the four-filar conductor wire 120 and the loops 141 of the tri-filar shock coil 126 is accomplished by plastically deforming a portion of the conductor wire 120 prior to assembly. The nominal or undeformed pitch $P_0$ between adjacent coils is shown in FIG. 9. The goal of the plastic deformation process is expand the pitch of at least two adjacent loops, in this case the loops 140 and 142, to the expanded pitch $P_1$ as shown in FIG. 10. The expanded pitch $P_1$ enables the loop 141 of the shock coil 126 to, in essence, be screwed together with the loops 140 and 142 of the conductor wire 120 so that the loop 141 is positioned between the loops 140 and 142 as shown in FIGS. 9, 10 and 11.

It is desirable to be able to visually verify the proper intertwining of the conductor wire 120 with the shock coil 126 after the outer crimp sleeve 137 is crimped to the inner crimp sleeve 138. To this end, the outer crimp sleeve 137 is provided with at least one viewing aperture 143 as shown in FIG. 9. Additional apertures may be provided with their particular number and spacing being largely a matter of design discretion. It is important that loops from both the conductor wire 120 and the shock coil 126 cross site of the crimp, so that both the wire 120 and the coil 126 are secured by a single crimp. One aperture 143 is adequate for this purpose, but a through bore is easier to manufacture and provides two, diametrically opposed apertures. The outer crimp sleeve 137 is crimped by conventional means, preferably circumferentially near the middle of the sleeve. Care must be taken to determine the depth of the crimp, avoiding buckling due to the apertures 143. Using the intertwined loops and single outer crimp sleeve to secure both the conductor wire 120 and the shock coil 126 makes it possible to shorten the overall length of the crimp sleeve assembly. In conventional crimp sleeve assemblies, described above, two outer crimp sleeves are used over a single inner crimp sleeve. The length of a conventional inner crimp sleeve is about 12 mm (0.5 inches). In contrast the inner crimp sleeve of this invention can be much shorter, preferably 7.2 mm (0.3 inches) or less, more preferably 6.6 mm (0.275 inches) or less. This makes insertion of a curved stylet much easier.

Figure 12:
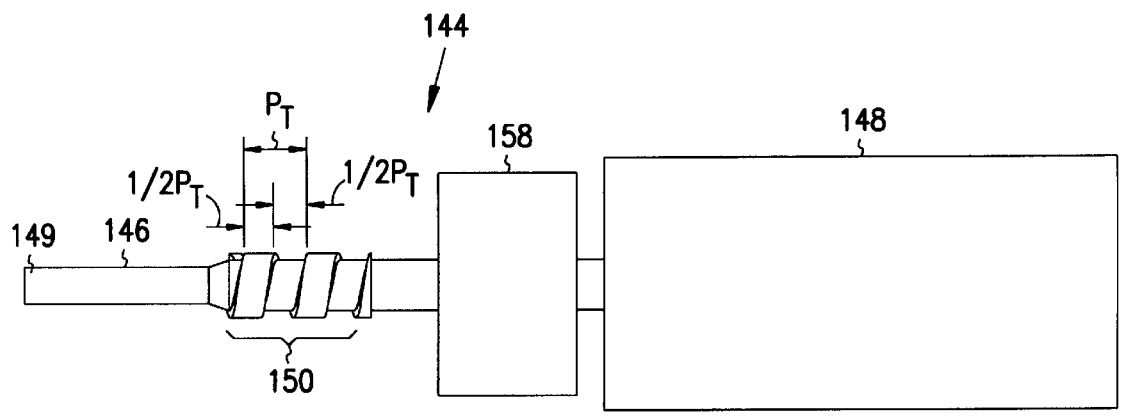
FIG. 12 is a side view of an exemplary embodiment of a wire coil spreader in accordance with the present invention.
Figure 13:
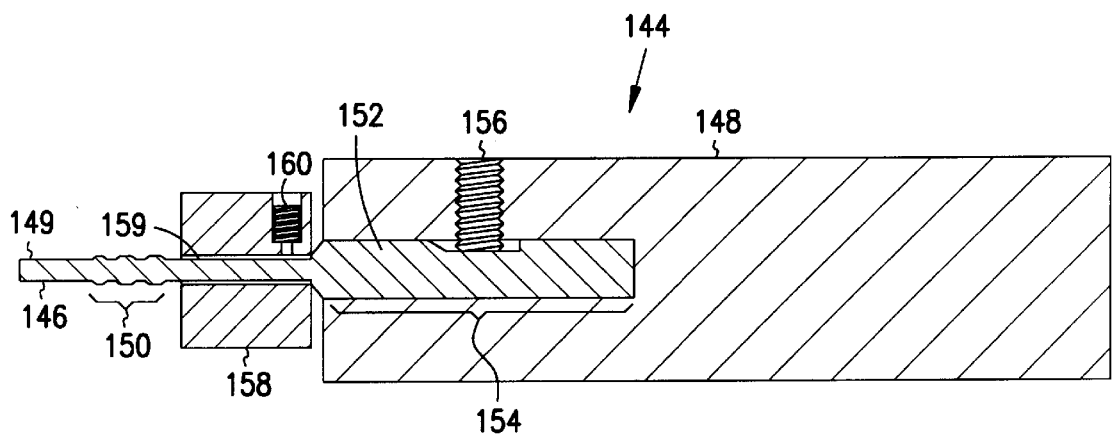
FIG. 13 is a cross-sectional view of the coil spreader shown in FIG. 12 in accordance with the present invention.

The deformation of the conductor wire 120 to achieve the desired pitch $P_1$ of the sets of loops 140 and 142 may be accomplished using a coil spreader 144, an exemplary embodiment of which is depicted in FIGS. 12 and 13. FIG. 12 is a side view of the coil spreader 144 and FIG. 13 is a sectional view of the coil spreader 144. The coil spreader 144 includes a mandrel 146 that is secured to a handle 148. The distal end 149 of the mandrel 146 is provided with a set of external threads or grooves 150 that are cut or otherwise formed in the mandrel 146 with a pitch direction, that is, left-handed or righthanded, that matches the pitch direction of the conductor wire 120. The grooves 150 are formed with a pitch $P_T$, and are helical and square so that the width of the root of each thread is equal to the width W of a loop of the conductor wire. In the case of the tri-filar conductor wire 12 the width W equals 3 times the diameter of a filar. The width of each crest is $P_T-W$. The pitch $P_T$ is related to the ultimately desired pitch $P_1$ of coils of the conductor wire 120 according to the expression:

$$P_T - X = P_1 \qquad \text{Equation}$$

where X is the anticipated elastic recovery of the conductor wire 120 following removal from the mandrel 146.

The distal end 149 is provided with an outer diameter that is just slightly less than the inner diameter of the conductor wire 120 to enable the conductor wire 120 to be readily slipped over the distal end 149. The proximal end 152 of the mandrel 146 is positioned in a bore 154 in the handle 148 and secured thereto by a set screw 156. A collar 158 is positioned over the mandrel via in internal bore 159 and is provided with a set screw 160 that is designed to engage the conductor wire 120 as described below.

Figure 14:
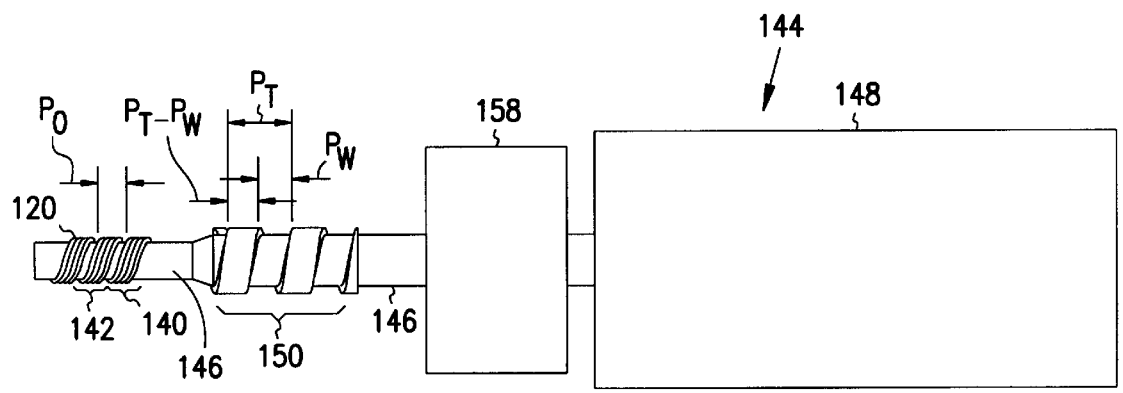
FIG. 14 is a side view like FIG. 12 showing a conductor wire positioned thereon prior to coil spreading in accordance with the present invention.
Figure 15:
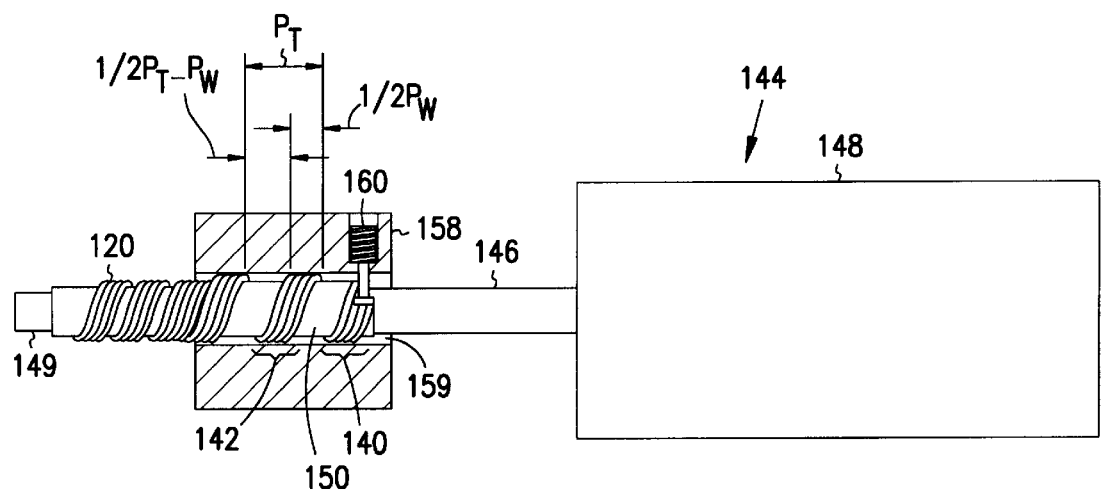
FIG. 15 is a view like FIG. 14 depicting the wire after coil spreading in accordance with the present invention.

The coil spreading operation may be understood by referring now to FIGS. 14 and 15, which are side views like FIG. 12 prior to and during the engagement of the threads 150 by the conductor wire 120. Referring initially to FIG. 14, the conductor wire 120 is slipped over the mandrel 146. At this point, the conductor wire 120 has a nominal pitch $P_0$ defined generally by the spacing between the fourth filar of one loop and the fourth filar of the next adjacent loop. As noted above, the threads 150 are formed with a pitch $P_T$ and are helical and square. Referring now to FIG. 15, the collar 158 is slipped over the threads 150 and the set screw 160 is tightened until it bottoms out on the mandrel 146. The collar 158 prevents the loops 140 and 142 from slipping out of the grooves 150 during advancement through the threads 150. The conductor wire 120 is advanced until the distal end of the loop 140 engages the threads 150. At this point, the conductor wire 120 is rotated according to the pitch direction of the threads 150, in this case counterclockwise. As the conductor wire 120 is rotated, the adjacent loops 140 and 142 are spread apart by the threads 150 and plastically deformed to assume a new pitch which is approximately $P_T$. The conductor wire 120 may be rotated until the end thereof abuts the side of the set screw 160. To remove the wire 120 from the grooves 150, the collar 158 is rotated to unscrew the loops 140 and 142 from the threads 150. As the collar 158 is rotated the set screw 160 pushes against the end of the loop 140 to unscrew the wire 120 from the mandrel 146. If necessary, the set screw 160 may be loosened slightly to enable free rotation of the collar 158. The plastic deformation of the loops 140 and 142 is almost instantaneous. Thus, the conductor wire 120 may be spiraled off the mandrel 146 without delay.

The spreading of the loops 140 and 142 will not result in complete plastic deformation. Instead, the loops 140 and 142 will undergo some recovery of magnitude X upon removal from the mandrel 146. Accordingly, the threads 150 are cut such that $P_T-X$ is approximately equal to the desired final pitch $P_1$ of the coils 140 and 142.

The detailed structure of the branch assembly 100 may be understood by referring again to FIG. 7. The branch assembly 100 includes a branch body 162 that is slipped over and glued around the segments 96 and 98 and the insulating sleeve 94 with a biocompatible medical grade adhesive. The branch body 162 is designed to provide a biocompatible, electrically insulating and readily moldable junction structure. Accordingly, the branch body 162 may be composed of a variety of biocompatible moldable insulating materials, such as silicone, polyurethane, or the like.

A crimp assembly 164 is positioned in the branch body 162 in generally longitudinal alignment with the segment 98 and the insulating sleeve 94. The crimp assembly 164 includes an outer crimp sleeve 166 positioned around and crimped to an inner crimp sleeve 168 to mechanically and electrically connect the conductor wire 120 to the conductor wire 122. The outer and inner crimp sleeves 166 and 168 may be substantially identical to the outer and inner crimp sleeves 137 and 138 shown in FIG. 9.

The wires 120 and 122 are connected to enable bipolar pacing. Pacing pulses generated by the cardiac stimulator 112 are transmitted to the tip electrode 132 (see FIG. 6) via the connector pin 108 and the conductor wire 133. Return pulses from myocardial tissue during pacing are routed back to the cardiac stimulator 112 through the annular contact 110 (see FIG. 6). The pathway for return pulses from myocardial tissue back to the annular contact 110 is through the shock coil 126, the conductor wire 120, and finally the conductor wire 122. The conductor wire 122 may take on a variety of configurations, such as single filar, multi-filar or the like and may be composed of the same types of materials used to fabricate the conductor wire 120. In an exemplary embodiment, the wire 122 is an uncoated, coiled three-filar wire composed of.

The engagement between the conductor wire 122 and the conductor wire 120 via the crimp assembly 164 is substantially identical to the configuration depicted in FIGS. 8, 9 and 10 in conjunction with the crimp assembly 125. The loops of the conductor wire 120 are spread as described above in conjunction with FIGS. 12, 13, 14 and 15 so that the loops of the tri-filar conductor wire 122 may be intertwined therewith at 172 and 174. First, the outer crimp sleeve 166 is placed around the conductor wire 120. Next, the conductor wire 120 is unfurled proximal to the outer crimp sleeve 166 and a coiled proximal segment is positioned in longitudinal alignment, off set from the distal part of the conductor wire 120. The unfurling establishes sections 176 of the filars in the branch body 162 that are shown in phantom. The coil spreader 144 is used to spread the loops of the area of the conductor wire 120 marked 164 in FIG. 7. With the handle 148 and collor 158 on the distal end 149 of the coil spreader 144, the loops at the distal end of the second conductor wire 122 are spread. The two wires 120, 122 are intertwined by threading the wires together such that a loop of the wire 122 lies between two adjacent loops of the conductor wire 120. On inner crimp sleeve 168, carried on a mandrel or rod (not shown) is passed within the conductor wire 122 to the junction area 164. The inner crimp sleeve 168 may be secured in place with a dab of medical adhesive. The outer crimp sleeve 166 is brought over the inner crimp sleeve 168 and within the junction area 164. As with the outer crimp sleeve 137, this sleeve also has a viewing aperture, in the form of a through bore. With loops from both wires 120, 122 positioned between the crimp sleeves 164, 166 a single circumferential crimp secures both wire. As described above since a single outer crimp sleeve is used to secure both wires 120, 122, the length of the crimp sleeve assembly can be reduced from 12 mm (0.5 inches) to 7.2 mm (0.3 inches) or less, more preferably 6.6 mm (0.275 inches) or less.

The conductor wire 132 that is connected distally to the tip electrode 130 shown in FIG. 6, passes through the branch body 162 and the inner crimp sleeve 168 and through the sleeve 133 that is positioned inside the segment 98 and is designed to electrically insulate the conductor wire 132 from the conductor wire 122.

The crimp assemblies 125 and 164 (see FIGS. 7 and 9) substantially reduce the length of rigid tubing through which the implanting physician must traverse a stylet during implantation. The result is less resistance to passage of the stylet, less potential for buckling of the stylet, and a better tactile response for the physician.

The foregoing illustrated embodiments included the union of a shock coil 126 and a conductor wire 120 (see FIGS. 6, 7 and 9). However, the skilled artisan will appreciate that the crimp assemblies 125 and 164 may be used to join a myriad of different types of conductor wires, either in a branched lead as shown, or in a lead incorporating a single insulating lead sleeve.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead, comprising:

a connector for coupling to a cardiac stimulator;

an inner crimp sleeve;

an outer crimp sleeve crimped around the inner crimp sleeve;

a first conductor wire electrically coupled to said connector having at least a first loop and a second loop; and a second conductor wire having a third loop, the first and second conductor wires being spiraled together so that the third loop is positioned between the first and second loops at least one of said first and second loops and said third loop being crimped between the inner crimp sleeve and the outer crimp sleeve.

2. The cardiac lead of claim 1, wherein the first conductor wire comprises a conductor coated with an insulating jacket.

3. The cardiac lead of claim 2, wherein the conductor comprises a plurality of conducting filaments.

4. The cardiac lead of claim 1, wherein the second conductor wire has a plurality of loops electrically exposed so as to be capable of making electrical contact with cardiac tissue.

5. The cardiac lead of claim 4, wherein the plurality of loops are coated with iridium oxide.

6. The cardiac lead of claim 4, wherein the conductor wire has three filars.

7. The cardiac lead of claim 1, wherein the outer crimp sleeve has an aperture to enable viewing of the third coil.

8. The cardiac lead of claim 7, wherein said operature comprises a through bore.

9. The cardiac lead of claim 7, wherein a single crimp secures both said first and second conductor wires.

10. The cardiac lead of claim 1, wherein said inner crimp sleeve and said outer crimp sleeve, as assembled, have a length of 7.2 mm (0.3 inches) or less.

11. The cardiac lead of claim 10, wherein said length is 6.6 mm (0.275 inches) or less.

12. The cardiac lead of claim 1, comprising a cardiac stimulator for connection to the connector.

13. A cardiac lead, comprising:

a first connector and a second connector coupled to a branch assembly;

a first conductor wire coupled to the first connector and having at least a first loop and a second loop; and a second conductor wire coupled to the second connector and having at least a third loop, the first and second conductor wires being spiraled together so that the third loop is positioned between the first and second loops and, at least one of said first and second loops and said third loop being, crimped between the inner crimp sleeve and the outer crimp sleeve, an inner crimp sleeve positioned in the branch assembly adjacent said loops and;

an outer crimp sleeve crimped around the inner crimp.

14. The cardiac lead of claim 13, further comprising, a third conductor wire having a fourth loop, the first conductor wire having a fifth loop and a sixth loop, the first and third conductor wires being spiraled together so that the fourth loop is positioned between the fifth and sixth loops and a second inner crimp sleeve adjacent said fourth, fifth and sixth loops, a second outer crimp sleeve crimped around said second inner crimp sleeve, at least one of said fifth and sixth loops and said fourth loop being crimped between the third sleeve and the fourth sleeve.

15. The cardiac lead of claim 14, wherein the third conductor wire has a plurality of loops electrically exposed so as to be capable of making electrical contact with cardiac tissue.

16. The cardiac lead of claim 15, wherein the plurality of loops are coated with iridium oxide.

17. The cardiac lead of claim 13, wherein the first conductor wire comprises a conductor coated with an insulating jacket.

18. The cardiac lead of claim 17, wherein the conductor comprises a plurality of conducting filaments.

19. The cardiac lead of claim 13, wherein said inner crimp sleeve and said outer crimp sleeve, as assembled, have a length of 7.2 mm (0.3 inches) or less.

20. The cardiac lead of claim 19, wherein said length is 6.6 mm (0.275 inches) or less.

21. The cardiac lead of claim 13, wherein said outer crimp sleeve has an aperture to enable viewing of the third coil.

22. The cardiac lead of claim 21 wherein said aperture comprises a through bore.

23. The cardiac lead of claim 21, wherein a single crimp secures both said first and second conductor wires.

* * * * *